(12) United States Patent
Chandran

(10) Patent No.: US 11,672,822 B2
(45) Date of Patent: Jun. 13, 2023

(54) PREVENTATIVE MANNOSE THERAPY AND TREATMENT OF VIRAL INFECTIONS USING MANNOSE-CONTAINING COMPOSITIONS

(71) Applicant: Preethi Chandran, Washington, DC (US)

(72) Inventor: Preethi Chandran, Washington, DC (US)

(73) Assignee: HOWARD UNIVERSITY, Washington, DC (US)

( * ) Notice: Subject to any disclaimer, the term of this patent is extended or adjusted under 35 U.S.C. 154(b) by 802 days.

(21) Appl. No.: 16/465,688

(22) PCT Filed: Dec. 1, 2017

(86) PCT No.: PCT/US2017/064275
§ 371 (c)(1),
(2) Date: May 31, 2019

(87) PCT Pub. No.: WO2018/102722
PCT Pub. Date: Jun. 7, 2018

(65) Prior Publication Data
US 2020/0016192 A1    Jan. 16, 2020

Related U.S. Application Data

(60) Provisional application No. 62/429,136, filed on Dec. 2, 2016.

(51) Int. Cl.
| | | |
|---|---|---|
| A61K 31/7004 | (2006.01) | |
| A61K 31/7016 | (2006.01) | |
| A61K 31/738 | (2006.01) | |
| A61K 9/51 | (2006.01) | |

(52) U.S. Cl.
CPC .......... *A61K 31/738* (2013.01); *A61K 9/5146* (2013.01)

(58) Field of Classification Search
CPC ........................... A61K 31/738; A61K 9/5146
See application file for complete search history.

(56) References Cited

U.S. PATENT DOCUMENTS

| | | |
|---|---|---|
| 2007/0286896 A1 | 12/2007 | Yamazaki |
| 2008/0226684 A1* | 9/2008 | Peppas |
| 2010/0028559 A1 | 2/2010 | Yan |
| 2014/0220346 A1 | 8/2014 | Heller |
| 2016/0095820 A1 | 4/2016 | Peppas |
| 2016/0106852 A1 | 4/2016 | Yeoman |

OTHER PUBLICATIONS

Duran-Lobato et al., Surface-Modified P(HEMA-co-MAA) Nanogel Carriers for Oral Vaccine Delivery: Design, Characterization, and In Vitro Targeting Evaluation, Biomacromolecules, 2014, vol. 15, No. 7, pp. 2725-2734.
Patent Cooperation Treaty, International Search Report issued in International Application No. PCT/US2017/064275, dated Feb. 21, 2018, 2 pp.
Pubchem, Compound Summary for CID 870, Jun. 23, 2005, 18 pp., https://pubchem.ncbi.nlm.nih.gov/compound/870.

* cited by examiner

*Primary Examiner* — Alma Pipic
(74) *Attorney, Agent, or Firm* — Sughrue Mion, PLLC

(57) ABSTRACT

Methods and compositions are provided for preventing and/or treating infection by disrupting interactions at or near the surface of mannosylated pathogens or other pathogens exhibiting carbohydrate-carbohydrate self-interaction, thus enhancing the immune system's ability to recognize and destroy such pathogens. In some forms, carrier molecules are provided to delivering polymers or other molecules capable of disrupting intra-cellular interaction and/or self-interaction of surface markers on cells.

3 Claims, 1 Drawing Sheet

PREVENTATIVE MANNOSE THERAPY AND TREATMENT OF VIRAL INFECTIONS USING MANNOSE-CONTAINING COMPOSITIONS

CROSS-REFERENCE TO RELATED APPLICATIONS

This application is a U.S. national phase application filed under 35 U.S.C. § 371 of International Application PCT/US2017/064275, filed Dec. 1, 2017, designating the United States, which claims priority from U.S. Provisional Application No. 62/429,136, filed Dec. 2, 2016, both of which are incorporated herein by reference in their entirety.

BACKGROUND

Lethal viruses like Ebola, Marburg, SARS, Dengue, and HIV contain high amounts of the sugar-residue mannose in their cell wall. Mannose-binding lectins in the bloodstream or on macrophages recognize these mannose residues and trigger the innate pathway of the immune system which operates in the immediate hours and days following infection. It has been proposed to introduce concentrated sources of lectins in the body to bind mannose-containing viruses, increasing recognition of the virus by the host's immune system. Mice given high doses of mannose-binding lectin have been shown to survive ebola infection and become immune to reinfection. In other words, effective recognition of the pathogen mannose by host lectins appears to enhance resistance to infection.

Addition of free mannose has also been recognized to prevent lectins from binding to virus. For instance, cranberry juice is often recommended as a treatment for urinary tract infections, with mannose from the cranberry juice preventing mannose-containing viruses from sticking to the inner walls of the bladder.

SUMMARY

It has been found that when mannose residues are present in clusters on a surface of a pathogen, they have strong tendencies of self interaction, causing mannose residues to bind to one another and preventing other molecules, such as lectins, from binding to the mannose residues. Mannose clusters also appear to build a 'moat' of structured water over them interfering with access to the mannose residues. Abeyratne-Perera and Chandran, "Mannose Surfaces Exhibit Self-Latching, Water Structuring, and Resilience to Chaotropes: Implications for Pathogen Virulence," Langmuir. 2017 Sep. 12; 33(36):9178-9189. The self-stickiness and water-structuring properties of mannose clusters may obstruct lectins from accessing mannose residues and triggering the immune system. Together, the mannose-mannose interactions and water structuring created by mannose-containing antigens create a "shield" or barrier inhibiting recognition of the pathogen by molecules that bind to mannose.

Described herein are methods and compositions for preventing and/or treating infection by disrupting mannose self-interactions and water structuring, thus enhancing lectin recognition and/or the immune system's ability to recognize and destroy pathogens with mannose surface markers. In some forms, delivering polymers capable of disrupting self-interaction of mannose surface markers on cells (such as mannose, mannobiose, or mannose-containing polymers which may be linear or branched), preferably free forms thereof, to a target area prior to contact with a pathogen may be used to enhance lectin recognition of pathogen mannose by disrupting the self-stickiness and water-structuring of mannose clusters in the pathogen capsule. Mannose receptors on immune cells, macrophages, and dendritic cells are also more easily able to recognize the pathogens when mannose self-adhesion and water structuring are reduced. Free forms of mannobiose interfere with ordered packing between anchored mannose residues, disrupting both self-stickiness and water-structuring. In this manner, the immune response to the initial introduction of the pathogen will be augmented, preventing or reducing the infection of cells by the pathogen.

In one form, mannose-coated nanogels filled with mannobiose cargo may be released into the bloodstream via oral, intradermal, subcutaneous, or intramuscular delivery, where they are ready to bind or adhere to pathogens with a mannose-rich exterior. In some forms, the nanogels are about 5-200 nm size, and in some embodiments may be coated with mannose polymers and/or other oligosaccharides and ligands for cell surface receptors. Nanogels stick and spread on pathogen surfaces via self-adhesion of mannose clusters, releasing the mannobiose cargo. This results in localized delivery of free mannobiose in high concentrations in order to disrupt both mannose interactions within the pathogen (e.g. within a viral capsule) and the mannose interactions between the nanogel and the pathogen, rendering the pathogen more amenable for lectin recognition without releasing substantial amounts of mannobiose separate from the pathogen clusters that could compete for binding of lectins and reduce pathogen recognition. Preferably, nanogels are introduced into an area where lectins are available to bind pathogens that pass nearby and become 'visible.'

In some forms, a broad-spectrum preventative dose of a nanogel containing mannose and/or mannobiose and/or mannose polymers (e.g. 3-12 monomers) may be used to prime incoming pathogens to be susceptible to immune recognition. The nanogel may be any cross-linked hydrophilic polymer network of about 5 nm to hundreds of nm, for instance 10 nm to 200 nm. The nanogels may be administered in an amount effective for preventing one or more mannosylated pathogens from infecting the host and causing a diseased condition. The nanogels may be coated with dangling polymers of mannobiose (e.g. containing 2-9 monomers) to latch on to mannose patches on pathogens. In some forms, the gels release moieties to achieve local surface concentrations of 2-10 mM of mannose-shield-disrupting agents. In contrast to vaccines or lectin boosts, which prime the host to fight infection, or treatments that attack pathogens directly with drugs or small molecules, this treatment attacks the pathogen indirectly and manipulates the pathogen in order to render it more vulnerable to a normal immune system response.

In another form, a dosage of mannose and/or mannobiose containing nanogel is administered in an amount effective for treating a disease caused by a mannosylated pathogen. The treatment is advantageous in that it is effective against a broad spectrum of diseases, such as Ebola, Marburg, SARS, Dengue, and/or HIV. Such a treatment may optionally be used in combination with lectin therapy and/or drug treatments targeting a specific pathogen. It can be used to prime the body before exposure to such agents. Cancer cells like that of breast cancer also have a layer of mannose on their surface which could relate to them evading the immune system. The proposed therapy can also target cancer cells and render them more vulnerable to the immune system.

In addition, or alternatively, the nanogels may include other small molecules (<5 kDa) which disrupt hydrogen bonding, are uncharged, and do not interfere with mannose-lectin binding.

In some forms, mannose and/or mannobiose is delivered by a Polyethyleneimine (PEI) nanogel. Preferably, the nanogels are mannose-coated and carry a cargo effective for reducing self-adhesion and water structuring of the pathogen's mannose residues, such as free mannose or mannobiose. The nanogels are configured to bind to mannosylated surfaces of the pathogen and release their mannose or mannobiose cargo when inter-polymer interactions are disturbed by the nanogel spreading on the pathogen surface (or a pathogen-like surface). Other polymers from which nanogels may be formed include, for instance, PEG and polylysine. The nanogel polymers may be modified, or in some forms may be modified with graft molecules such as PEG, oligosaccharides, and/or ligands.

The preventative and therapeutic treatments discussed herein can be effective against a variety of pathogens, including fungi, viruses, and bacteria. For instance, *Cryptococcus neoformans* is a fungal pathogen that causes meningitis, an opportunistic infection in immune-compromised individuals. Its polysaccharide capsule contains one- to two-thirds mannose, and self-interaction has implications for virulence as well as hydration, biofilm, and immune-recognition properties attributed to the capsule. Viruses, particularly lethal ones like Ebola, Marburg, SARS, Dengue, and HIV also have high mannose content in their cell wall.

DETAILED DESCRIPTION

Figure 1:
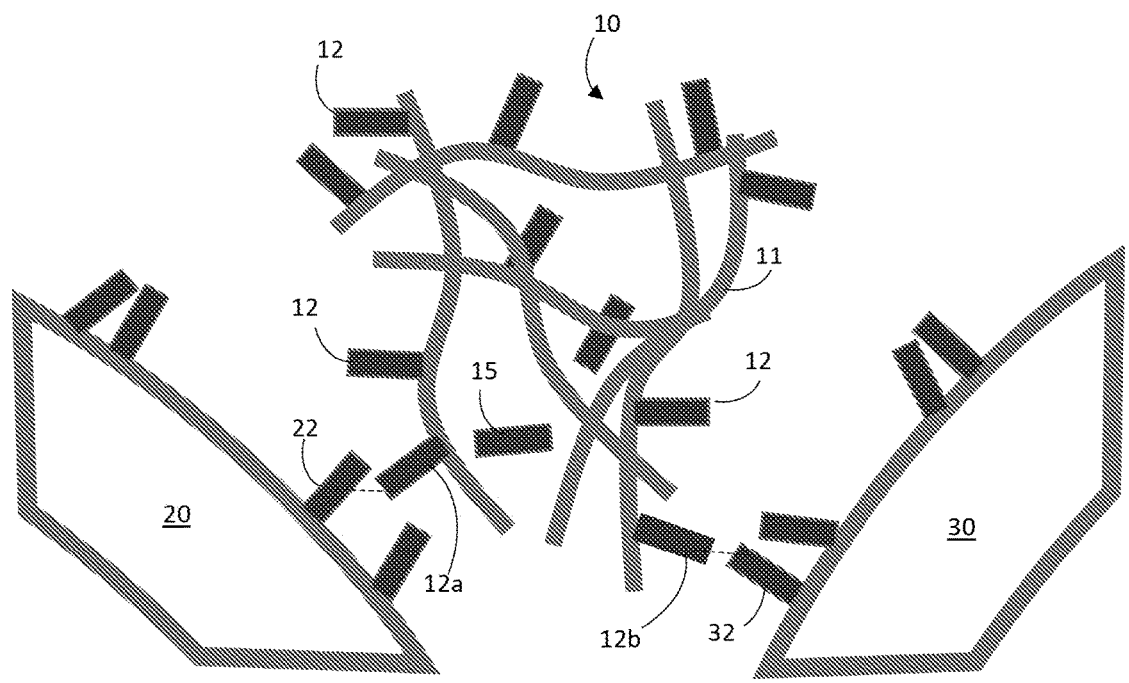
FIG. 1 is an illustration showing a nanogel according to some embodiments encountering portions of two pathogens.

Generally speaking, and pursuant to various embodiments, molecules and/or compositions are introduced to disrupt local interaction between mannose residues present on surfaces of pathogens, especially where the mannose residues are highly concentrated and as a result have strong tendencies of self-interaction. In some forms, compositions are provided comprising nanogel particles carrying or bonded to mannose or mannose-containing polymers. In some form, such nanogel particles are introduced into a patient's body to prevent or treat infections caused by one or more fungi or viruses. The nanogels increase interactions between the pathogens and various immune cells, allowing the immune system to more efficiently dispose of mannose-containing pathogens.

Pathogens containing mannose or similar molecules on their surface, especially fungi and viruses where the number and variety of antigens is relatively low, may become difficult to detect by antibodies and other molecules and cells of the immune system as the mannose molecules tend to interact with one another or themselves through carbohydrate-carbohydrate interactions. This is particularly true in fungi and viruses, where the number of different types of glycans on the outer surface are relatively low. The clusters are internally self-sticky and outside probes can require several nanoNewtons of force to break through, effectively hiding the presence of these mannose residues and preventing their recognition as antigens by the host's immune system. The self-affinity of mannose is surprising because, unlike many glycans where carbohydrate-carbohydrate interactions have been observed and measured, mannose is not charged.

For instance, fungal cell walls contain only a limited selection of sugars linked to lipids and proteins on their cell walls, and mannose may comprise as much as 20-50% of these sugars, often distributed toward the outer cell surface. Mannosylated proteins are critical for fungal viability, and appear to be recognized by receptors for the cell-mediated pathway of the mammalian immune system. Mannose is also present extensively in polysaccharide capsules covering cell walls of pathogenic fungi. Patches of surface mannose levels also appear to be present on some viruses, such as filoviruses like Ebola, Marburg, SARS, Dengue, and HIV. Carbohydrate-carbohydrate interaction forces appear to be much stronger (i.e. about three-fold) between glycans of the same type than between different types. Thus patches of mannose-containing surface antigens have the potential for strong self-interactions to the exclusion of interactions with structures that are not part of the pathogen.

Mannose clusters on pathogens also appear to build a 'moat' of structured water over them, extending for as much as 30 nms, and which resists the approach of outside probes. Thus, mannose antigens may effectively form a shield-type structure forming a barrier to recognition by immune receptors. Mannose sugars are present extensively on the outer surface of pathogenic viruses and fungi, and are normally detected by lectins of the immune system to initiate phagocytosis. Carbohydrate-carbohydrate interactions between mannose molecules on the pathogen surface, believed to be mediated by hydrogen bonding and ion-coordination between clustered and ordered glycans, can result in strong self-specific interactions (e.g. about 27 pN per mannose residue). The self-adhesion and water-structuring effects appear to be amplified at low salt concentrations.

Without wishing to be bound by theory, it appears that by delivering mannose-equipped nanogels to a localized area containing pathogens having mannose-containing surface antigens, carbohydrate-carbohydrate interaction and water-structuring by the antigens is disrupted and the antigens are made more accessible to mannose receptors on immune cells, macrophages, and dendritic cells. Free forms of mannobiose have been shown to interfere with ordered packing between anchored mannose residues, disrupting both self-stickiness and water-structuring. In this manner, the immune response to the initial introduction of the pathogen will be augmented, preventing or reducing the infection of cells by the pathogen.

Molecules capable of disrupting or interfering with mannose-mannose interactions and mannose-induced water structuring at or near pathogen surfaces, referred to herein as "mannose-shield-disrupting agents," may be employed to make mannose-containing surface features of pathogens more available and receptive to lectins, antibodies, and other molecules. In some forms, the mannose-shield-disrupting agents include mannose, mannobiose, or relatively short polymers made up of or containing mannose monomers (e.g. 3-12 monomers, some or all of which are mannose). Alternatively, mannose-shield-disrupting agents may be other molecules less than about 5 kDa that disrupt hydrogen bonding and are uncharged, such as lactose, glucose, mannitol, and other small mono or disaccharides. Advantageously, some such mannose-shield-disrupting agents do not interfere with mannose-lectin binding and do not bind with lectin, thereby rendering mannose antigens on pathogens more accessible but avoiding competitive binding with lectins.

In some forms, a sufficient amount of mannose-shield-disrupting agent is provided to achieve local surface concentrations of 2-10 mM of mannose-shield-disrupting agents. In some forms, a carrier containing mannose-shield-disrupting agents is provided so that the carrier releases the agents over time or upon encountering specific environmental conditions. In some forms, the carrier is a nanogel that releases moieties in order to achieve local surface concentrations of 2-10 mM of mannose-shield-disrupting agents.

In some forms, nanogels or other carriers are bonded with mannose-containing polymers and extend from the nanogel carrier as dangling polymers in order to interact with nearby mannose antigens. Mannose-containing polymers may be bonded to the nanogel structure using chemical bonds, and in some forms contain about 2 to 9 monomers. In some forms, the dangling polymers attached to nanogels consist essentially of from 2 to 9 mannose monomers. Less than 50% charge is preferable. Alternatively, or in addition, mannose-shield-disrupting agents may be provided as cargo to nanogel carriers, so that they are trapped by or held in association with the nanogel carrier in one conformation and released to the surrounding environment in another conformation. When provided as cargo, mannose polymers preferably contain 2-9 monomers, some or all of which are mannose.

Figure 2:
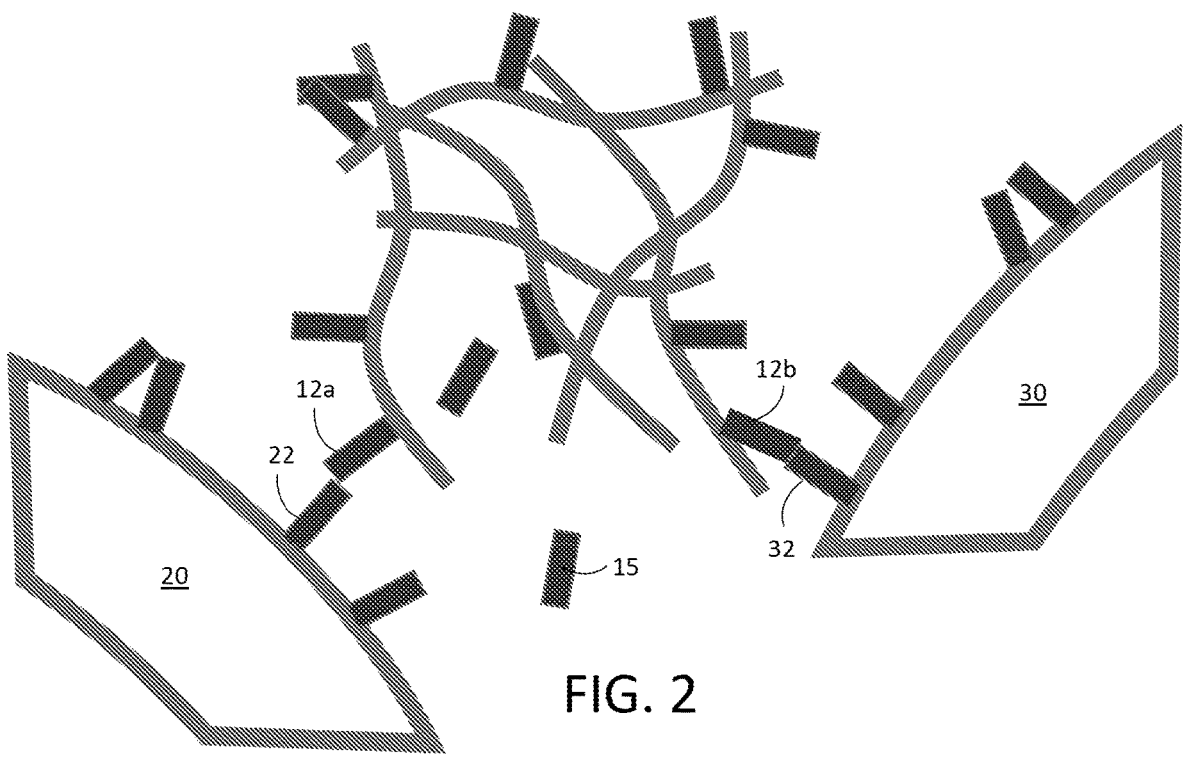
FIG. 2 is an illustration showing the nanogel of FIG. 1 releasing its cargo due to interactions with the pathogens.

FIG. 1 illustrates interaction between a nanogel 10 and portions of two pathogens 20 and 30. The Nanogel 10 comprises a plurality of polymers 11 including mannose-containing appendages 12. In addition, mannose-containing molecules 15 are held as cargo within the nanogel structure. As some of the appendages 12 begin interacting with the pathogens, for instance nanogel appendage 12a interacting with mannose-containing surface feature 22 of pathogen 20 and appendage 12 b interacting with mannose-containing surface feature 32 of pathogen 30, the nanogel structure may be spread by relevant movement between the pathogens 20 and 30, resulting in release of cargo 15 as shown in FIG. 2.

The mannose-coated nanogels and/or nanogels filled with mannose-containing cargo may be introduced into the body of a mammal orally, intradermally, subcutaneously, or intramuscularly, with or without a one or more excipients and/or other additives, for instance by ingestion or injection. The coated nanogels and/or released cargo can bind or adhere to pathogens with a mannose-rich exterior. In some forms, sticking and spreading of the nanogel on pathogen surfaces due to adhesion between dangling polymers of the nanogel and mannose-containing antigen clusters can cause release of the mannobiose cargo. In other embodiments, the nanogels may release mannobiose-containing cargo in reaction to changes in environmental conditions, causing shifting of the nanogel structure. This results in localized delivery of free mannose, mannobiose, or mannose polymer in high concentrations in order to disrupt both mannose interactions within the pathogen (e.g. within a viral capsule) and the mannose interactions between the nanogel and the pathogen, rendering the pathogen more amenable for lectin recognition without releasing substantial amounts of mannobiose separate from the pathogen clusters that could compete for binding of lectins and reduce pathogen recognition.

Mannose-coated and/or mannose-containing nanogels may be utilized as a preventative measure to prime incoming pathogens to be susceptible to lectin binding or other immune recognition. In some forms, the nanogels may be a cross-linked hydrophilic polymer network having a largest dimension of about 5 nm to hundreds of nm, preferably 10 nm to 200 nm. The nanogel may comprise crosslinked polyethylenimine, polyethylene glycol, and/or polylysine. In particular, the nanogel particles may comprise cross-linked linear polyethylenimine. In some forms, the polymers making up the nanogel may be cross-linked with an amine cross-linking agent such as glutaraldehyde. The preventative nanogels may be coated with dangling polymers containing mannose-shield-disrupting agents, with the dangling polymers preferably made up of 2-9 monomers that can be linear or branched. In some forms, the dangling polymers comprise 2-9 mannose monomers. In some forms, the nanogels are loaded with free mannose, mannose-containing compounds, and/or other mannose-disrupting agents that may be released by the nanogels. In some forms, the nanogels are loaded with a combination of mannose and mannobiose. In some forms, a sufficient amount of nanogel is delivered to achieve local surface concentrations of 2-10 mM of mannose or other mannose-shield-disrupting agent. In contrast to vaccines or lectin boosts, which prime the host to fight infection, or treatments that attack pathogens directly with drugs or small molecules, the treatments disclosed herein attack the pathogen indirectly and manipulate the pathogen in order to render it more vulnerable to a normal immune system response.

In another form, a dosage of mannose-coated nanogel or mannose, mannobiose, or mannose polymer containing nanogel is administered in an amount effective for treating a disease caused by a mannosylated pathogen. In some forms, 1-2 g of mannose is provided for treatment of urinary tract infections. These mannose treatment are advantageous in that they are effective against a broad spectrum of diseases, such as Ebola, Marburg, SARS, Dengue, and/or HIV. Such a treatment may optionally be used in combination with lectin therapy and/or drug treatments targeting a specific pathogen. Alternatively to, or in addition to, containing mannose disrupting agents, the nanogels may be loaded with other therapeutic agents, such as membrane disrupting molecules or other antiviral agents. In some forms, a sufficient amount of nanogel is delivered to achieve local surface concentrations of 2-10 mM of mannose or other mannose-shield-disrupting agent.

What is claimed is:

1. A nanogel particle comprising a plurality of cross-linked polymers, the particle further comprising a plurality of appendages extending therefrom, each appendage comprising mannobiose, and at least mannose, mannobiose, or a mannose-containing polymer is held within the nanogel particle,
   and
   the nanogel particle is configured to interact with a mannose-containing surface of a pathogen and release the at least mannose, mannobiose, or mannose-containing polymer.

2. The nanogel particle of claim 1, wherein the particle has a largest dimension of 10 nm to 200 nm.

3. A method of treating a mammal having a disease caused by a mannosylated pathogen, the method comprising administering an effective amount of the nanogel particle of claim 1 to the mammal.

* * * * *